United States Patent [19]

Grant

[11] 4,262,667

[45] Apr. 21, 1981

[54] VENTILATOR FOR USE IN MEDICAL APPLICATIONS

[76] Inventor: Graham C. Grant, 19 Lockley Parade, Roseville Chase, New South Wales, Australia, 2069

[21] Appl. No.: 68,397

[22] Filed: Aug. 21, 1979

[30] Foreign Application Priority Data

Aug. 24, 1978 [AU] Australia .............................. PD5650

[51] Int. Cl.³ ............................................ A61M 16/00
[52] U.S. Cl. .......................... 128/204.21; 128/205.14; 128/910
[58] Field of Search ...................... 128/205.14, 205.15, 128/205.16, 205.18, 204.24, 204.21, 204.23, 910; 251/129; 222/207, 209, 333, 334; 417/394, 412, 472, 473; 335/62, 247, 277

[56] References Cited

U.S. PATENT DOCUMENTS

| 3,339,545 | 9/1967 | Burchell | 128/205.14 |
| 3,385,294 | 5/1968 | Sabathie et al. | 128/204.21 |
| 3,932,066 | 1/1976 | Eyrick et al. | 417/328 |
| 3,951,137 | 4/1976 | Conkle et al. | 128/204.22 |
| 4,020,834 | 5/1977 | Bird | 128/205.14 |

FOREIGN PATENT DOCUMENTS 897230  5/1962  United Kingdom ..................... 335/247

Primary Examiner—Charles N. Hart
Assistant Examiner—David R. Sadowski
Attorney, Agent, or Firm—Ostrolenk, Faber, Gerb & Soffen

[57] ABSTRACT

An electrically powered mechanical ventilator for use in medical applications. The ventilator comprises a bellows-form expansible chamber which communicates with a gas inlet/delivery port and at least one electric motor which is energised to effect cyclic expansion and compression of the chamber by way of a motion translating mechanism. In a preferred form of the ventilator, two electric motors are mounted to a common shaft and means are provided for effecting cyclic energisation of the respective motors whereby the shaft is driven cyclically in opposite directions to effect the expansion and compression of the chamber.

12 Claims, 7 Drawing Figures

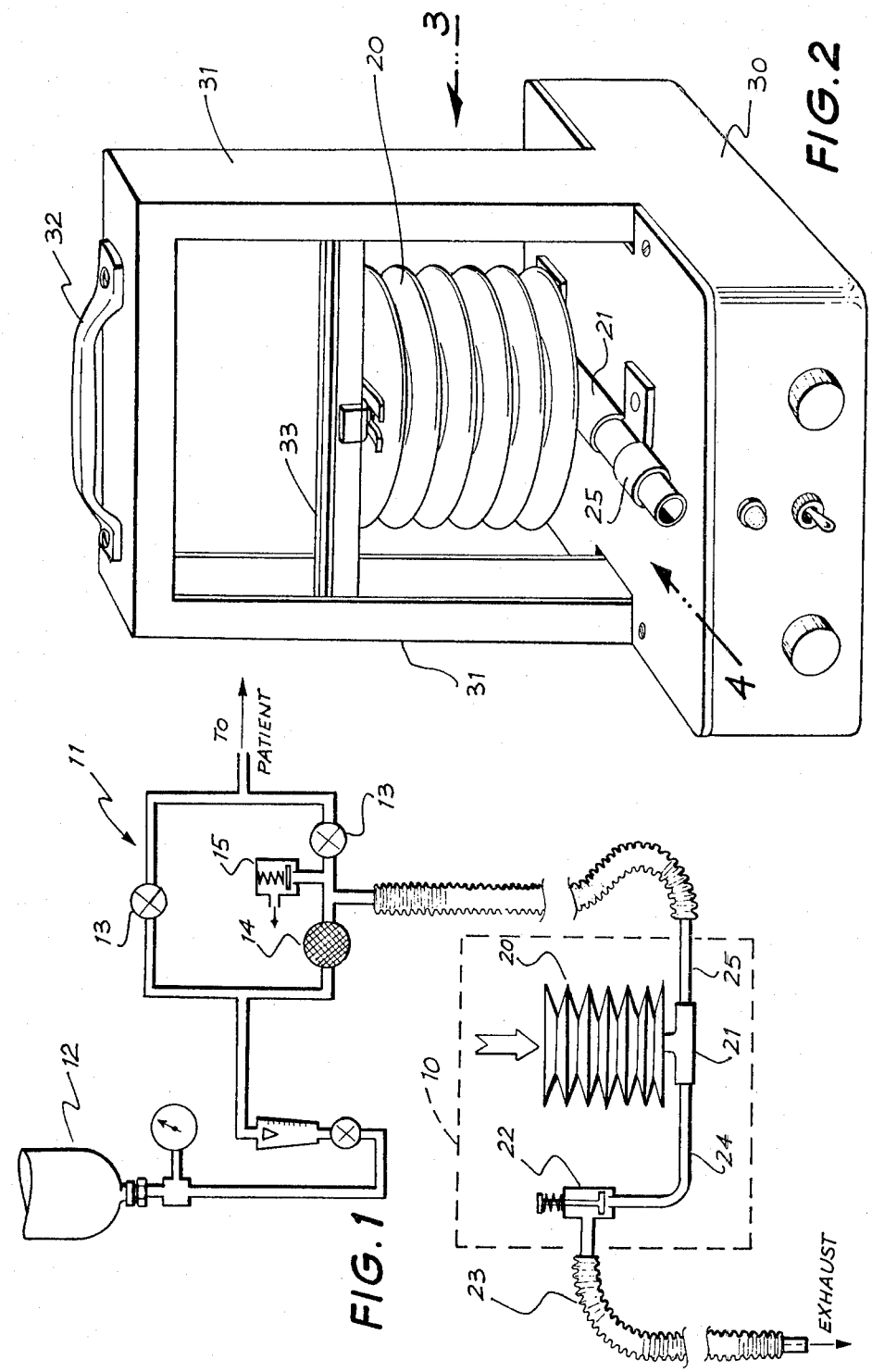

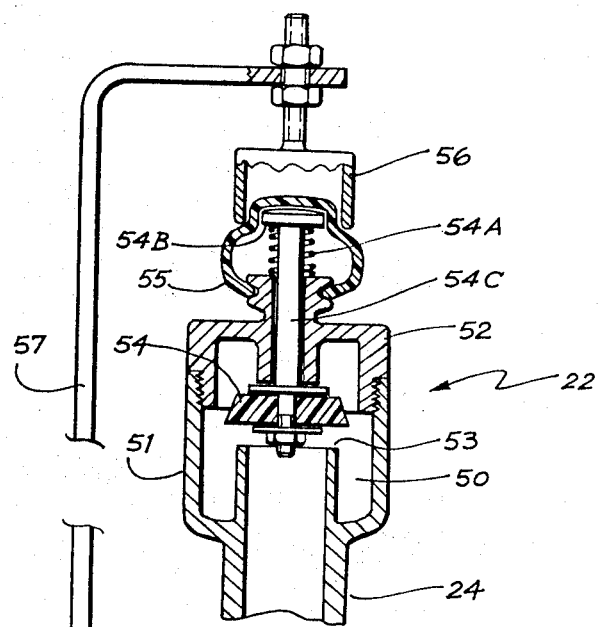
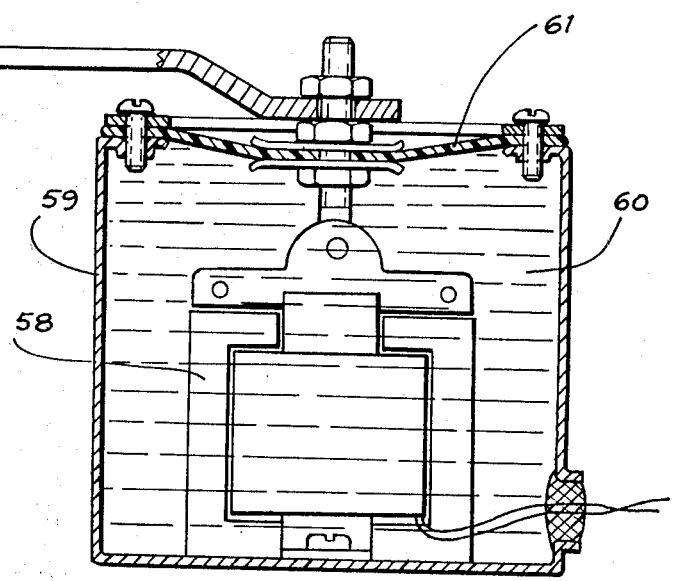
FIG. 6

VENTILATOR FOR USE IN MEDICAL APPLICATIONS

FIELD OF THE INVENTION

This invention relates to a mechanical respirator, alternatively and herein termed as "ventilator," for use in automatic ventilating of a patient's lungs. The ventilator may be used for human patients or for animals.

The ventilator may be employed either for respiratory therapy or in anaesthesia, and hence may be used for pumping air-oxygen-mixtures or oxygen or anaesthetic gases. However, for convenience and without any limiting intent, the ventilator which is the subject of the present invention is hereinafter described in the context of anaesthesia applications.

BACKGROUND OF THE INVENTION

Ventilators of various types, including manually operated, gas powered and electrically powered ventilators are well known and are customarily used in patient circuits incorporating a closed circuit, which includes a carbon dioxide absorber and gas direction control valves, or with a non-rebreathing valve, or with an unvalved T-piece (Ayre or Bain) type circuit in which rebreathing of exhaled gases does not occur. A comprehensive selection of known types of ventilators is described in a text by W. W. Mushin et al., "Automatic Ventilation Of The Lungs," Second Edition (1969), Blackwell Scientific Publications.

SUMMARY OF THE INVENTION

The ventilator in accordance with the present invention is of an electrically powered type.

Broadly defined, the ventilator of the present invention comprises an expansible chamber, a gas inlet/delivery port communicating with the chamber, two electric motors coupled to a rotatable shaft, means permitting energization of the motors, motion translating means coupling the shaft to the chamber and operable to impart compression strokes to the chamber responsive to energization of the motor, means for effecting expansion of the chamber following each compression stroke, and means for determining the extent of the expansion stroke and the compression stroke of the chamber.

PREFERRED FEATURES OF THE INVENTION

The present invention preferably provides a ventilator comprising an expansible chamber, a gas inlet/delivery port communicating with the chamber, first and second electric motors coupled to a rotatable shaft, means permitting energization of the motors whereby the shaft is driven cyclically in opposite rotational directions, motion translating means coupling the shaft to the chamber and operable to impart cyclic expansion and compression strokes to the chamber in dependence on the direction of rotation of the shaft, and means for determining the extent of the expansion stroke and the compression stroke of the chamber. Preferably, the length of at least one of the strokes is selectively variable.

In accordance with one preferred aspect of the invention the means for determining the expansion stroke of the chamber comprises means for adjustably timing the period of the expansion stroke imparted to the chamber, for effecting cessation of the expansion stroke after a predetermined time interval has elapsed and for effecting reversal of the direction of rotation of the shaft whereby the chamber is then caused to undergo a compression stroke. Then, the means for determining the extent of the compression stroke would comprise means for sensing a predetermined compression of the chamber and for effecting reversal of the direction of rotation of the shaft so that the chamber is then caused to undergo an expansion stroke.

In accordance with an alternative but less preferred form of the invention, the above defined functional arrangement may be reversed. Thus, the means stated for sensing the predetermined compression of the chamber may be employed for sensing a predetermined expansion stroke of the chamber, and the means stated for adjustably timing the expansion stroke would then be employed for adjustably timing the period of the compression stroke.

Cyclic rotation of the shaft in opposite directions is achieved by the use of the two motors, both of which having their rotors mounted to a common shaft. The respective motors are wound, energized or orientated so as to impart mutually opposite directions of rotation to the shaft, and when one motor is energized the other is not. This means that, whilst the rotor of one motor is delivering torque to the shaft, the rotor of the other motor will rotate substantially freely within its stator.

Except under conditions where a dwell time is introduced, this being hereinafter discussed, when current flow to a first one of the motors is terminated and is applied to the second motor, the starting torque of the second motor will be greater than that exerted by the free-wheeling first motor and will result in reversal being imparted to the direction of rotation of the shaft and the rotor of the first motor.

In order to permit the use of small-size motors, to achieve desired low speed compression and expansion strokes and to permit high torque delivery to the motion translating means from the small-size (and hence low torque) motors, a speed-reduction gearbox is preferably interposed between the motors' shaft and the motion translating means.

The motion translating means preferably comprises a link-chain or equivalent positive drive transmission mechanism which is connected to the output shaft of the gearbox by a sprocket and which is coupled to the expansible chamber by a driven arm.

The expansible chamber preferably comprises a bellows device which is concertinaed during the compression stroke.

Means may be provided for introducing an adjustable time delay (i.e. a dwell time or expiratory pause) into the ventilation operation following cessation of the expansion stroke and for delaying commencement of the next succeeding compression stroke. Thus, in addition to providing for a variable length expansion/compression stroke, the ventilator may conveniently be provided with a pseudo rate control. This is effectively achieved by adding the dwell time to the duration of the expansion stroke, the total period then being greater than the compression stroke duration.

In order to satisfy the conventional requirements for a so-called spill valve, the inlet/delivery port of the chamber may be connected to a T-piece fitting and a valve may be connected in circuit with one part of the T-piece. Valve control means would then be provided to effect closing of the valve during the period of the compression stroke of the chamber. The valve is preferably solenoid operated.

The invention will be more fully understood from the following description of a preferred embodiment of a ventilator for use in anaesthesia applications, the description being given with reference to the accompanying drawings.

BRIEF DESCRIPTION OF THE DRAWINGS

In the drawings,

FIG. 1 shows a schematic representation of the ventilator connected with a conventional type of closed circuit, the closed circuit in turn forming part of a patient circuit, FIG. 2 shows a perspective view of the ventilator, FIG. 6 shows a sectional elevation view of a portion of the ventilator as seen in the direction of section plane 6—6 of FIG. 3.

DETAILED DESCRIPTION OF THE INVENTION

Figure 3:
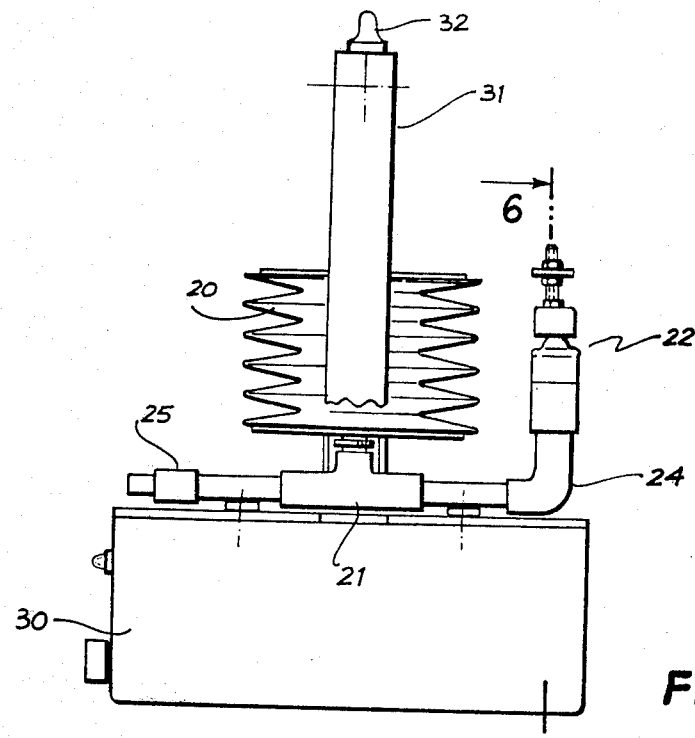
FIG. 3 shows a side elevation view of the ventilator as viewed in the direction of arrow 3 in FIG. 2.

The ventilator is designated by numeral 10 in FIG. 1 and it is shown connected to a closed circuit 11. The closed circuit is of conventional construction, is connected to a source 12 of anaesthetic gas, is connectable to a patient's lungs, includes the usual direction control valves 13, soda-lime $CO_2$ absorber 14 and blow-off valve 15, and forms no part of the ventilator per se of the invention.

The ventilator 10 has, as its principal features, a bellows-type expansible chamber 20, a T-connector 21 and a spill valve 22 which is connected to atmosphere or to a scavenger by way of a reservoir 23 in the form of a short length of tubing. One arm 24 of the T-piece 21 connects with the valve 22 and the other arm 25 is, in service, connected to the closed circuit 11.

The construction and operation of the ventilator 10 is now described in more detail with reference to FIGS. 2 to 7 of the drawings.

In general terms and as shown in FIGS. 1 and 2, the ventilator comprises a lower housing 30 which contains a drive mechanism, an upper channel-section frame 31 which is fixed to the housing and which carries a handle 32, a bridge 33 which extends between the two uprights of the frame 31 and which is movable up and down, and the bellows-type expansible chamber 20 which is removably connected to the bridge 33. The chamber 20 has an inlet/delivery port (not shown) in its under surface, and the T-piece 21 communicates with the interior of the chamber. The T-piece and its associated arms 24 and 25 is removably attached to the housing 30 and the arm 24 of the T-piece connects with the spill valve 22. In operation of the ventilator, the chamber 20 is expanded by an upward (expansion) stroke being imparted to the bridge 33 and is compressed by a downward (compression) stroke being imparted to the bridge.

Two motors, i.e. first and second motors 35 and 36 are mounted within the housing, the rotors of both motors being mounted to a common shaft 37. The shaft 37 is connected to the input of a step-down gearbox 38 which has an output shaft 39. The motors are both two-pole, single phase, split-phase induction motors, and the gearbox provides for an output shaft velocity of approximately 75 r.p.m. when the motors are operating under steady-state conditions. The motors are arranged and mounted to the shaft 37 so that, with the first motor 35 excited the shaft 37 rotates in one direction and with the second motor 36 excited the shaft 37 rotates in the opposite direction.

The output shaft 39 of the gearbox is fitted with a drive sprocket 40 and a similar, aligned, sprocket 41 is mounted within the channel-section side member of the frame 38. An endless link-chain 42 extends around and between the two sprockets. The upper sprocket is mounted to a live axle 43 to which an oppositely positioned third sprocket 44 is also mounted. A fourth, idler, sprocket 45 is located below the third sprocket, and a second endless link-chain 46 connects those two sprockets.

Figure 4:
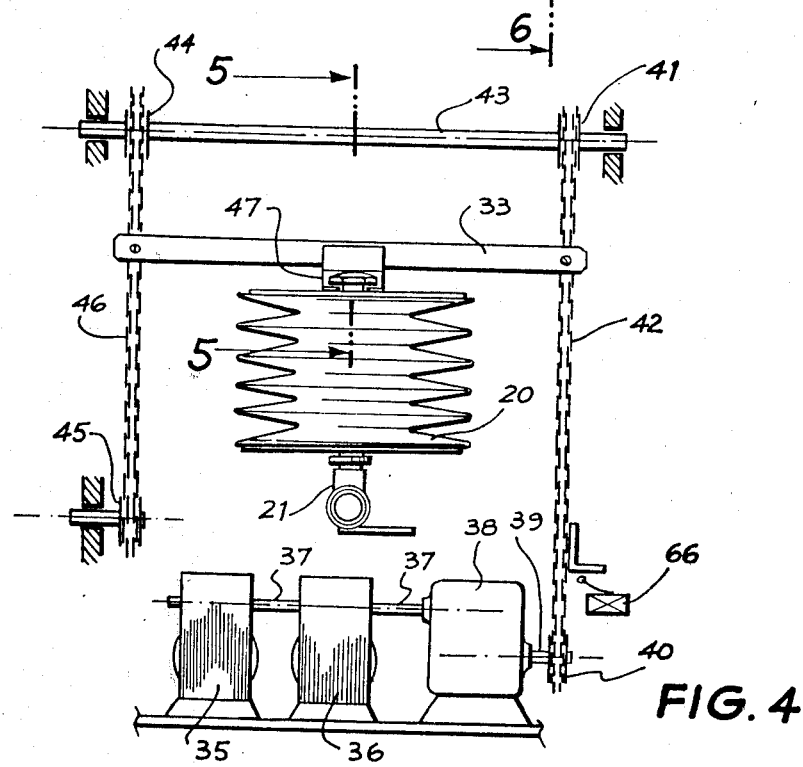
FIG. 4 shows an end elevation of the ventilator as viewed in the direction of arrow 4 in FIG. 2, the ventilator being illustrated with its casing and super structure removed for the purpose of showing drive mechanisms.
Figure 5:
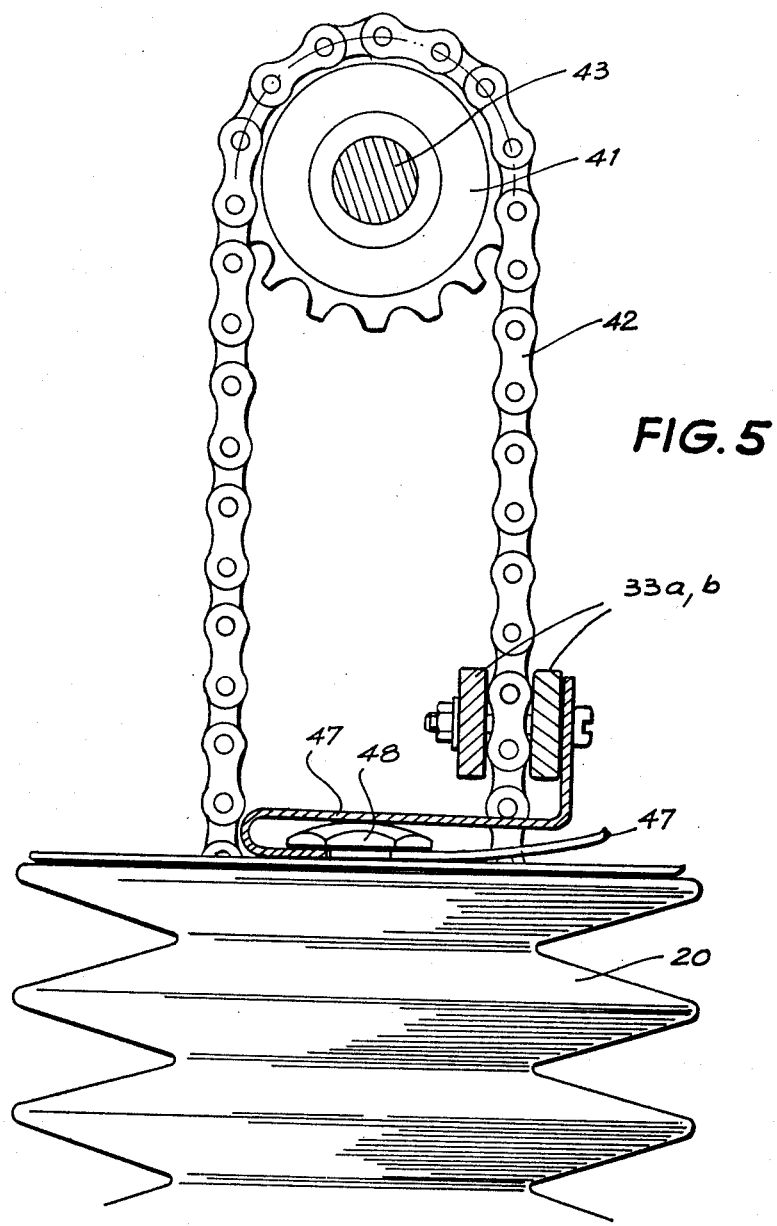
FIG. 5 shows a scrap view (on an enlarged scale) of an upper portion of the ventilator, the view being taken through section plane 5—5 as indicated in FIG. 4.

The bridge 33 is connected to and extends between one limb of each of the two chains 42 and 46, as shown in FIGS. 4 and 5. The bridge is driven up and down cyclically with cyclic rotation of the motor shaft 37 in forward and reverse directions. Limits are imposed on the up and down (expansion and compression) strokes of the bridge, as hereinafter described.

As shown in FIG. 5, the bridge 33 comprises two spaced-apart bars 33a and 33b which extend between and are connected to one limb of the link-chains 42 and 46. A slotted connector 47, in the form of a metal strip which is folded with a U-bend is screw fastened to the bridge bar 33a, and an upper structural portion 48 of the chamber 20 is slidably fitted into the slot in the connector 47. The structural portion 48 of the chamber is formed from metal and comprises a projection which is provided with a grooved recess for receiving the slotted connector 47.

The chamber 20 is removed from the main structure of the ventilator by disconnecting the T-piece 21 from the housing 30 and by sliding the upper end of the chamber away from the connector 47. This is facilitated by the inherent resiliency of the chamber material, typically a synthetic rubber.

Reference is now made to FIG. 6 of the drawings which shows a detailed view of the spill valve 22 and a solenoid actuator therefor.

The valve is formed as an extension of the T-piece limb 24 and it comprises a chamber 50 within a two-piece casing, the two parts 51 and 52 of which are screw connected. A valve seat 53 is formed within the casing part 51, and a normally-open valve member 54 overlies the valve seat. The valve member 54 is biased to the open position by a helical compression spring 54A, the spring locating between the casing part 52 and a flange 54B at the upper end of a stem portion 54C of the valve member. A flexible boot 55 enshrouds the upper end of the valve stem portion 54C and the boot is acted upon by a cap 56.

The cap 56 is coupled via a link 57 to a solenoid 58 which is located within the housing 30 and which, when energized, causes closure of the valve member 54 against the seat 53. The solenoid is energized to cause closure of the valve during the compression stroke of the chamber. Thus, relating to the arrangement shown in FIG. 1 of the drawings, the valve is closed during an inspiratory (compression) stroke of the chamber.

The valve chamber 50 (as shown in FIG. 6) communicates with the reservoir/exhaust line 23 as shown in FIG. 1.

The solenoid 58 is mounted within a casing 59 which is formed largely from metal or another oil impervious material, and the solenoid is immersed, at least to the level of its pole faces, in a bath 60 of oil. The casing 59 is fitted with a closure 61 which is formed from a synthetic rubber or other resilient material, and a connection is made between the solenoid and the link 57 by way of the closure 61. Thus, during opening and closing movements of the solenoid, consequential to its de-energization and energization respectively, the closure 61 is caused to flex so that the link 57 is moved upwardly and downwardly.

The casing 59 is located within the housing 30.

The solenoid is mounted in the manner as above described so as to achieve attenuation of noise produced during actuation of the solenoid.

Figure 7:
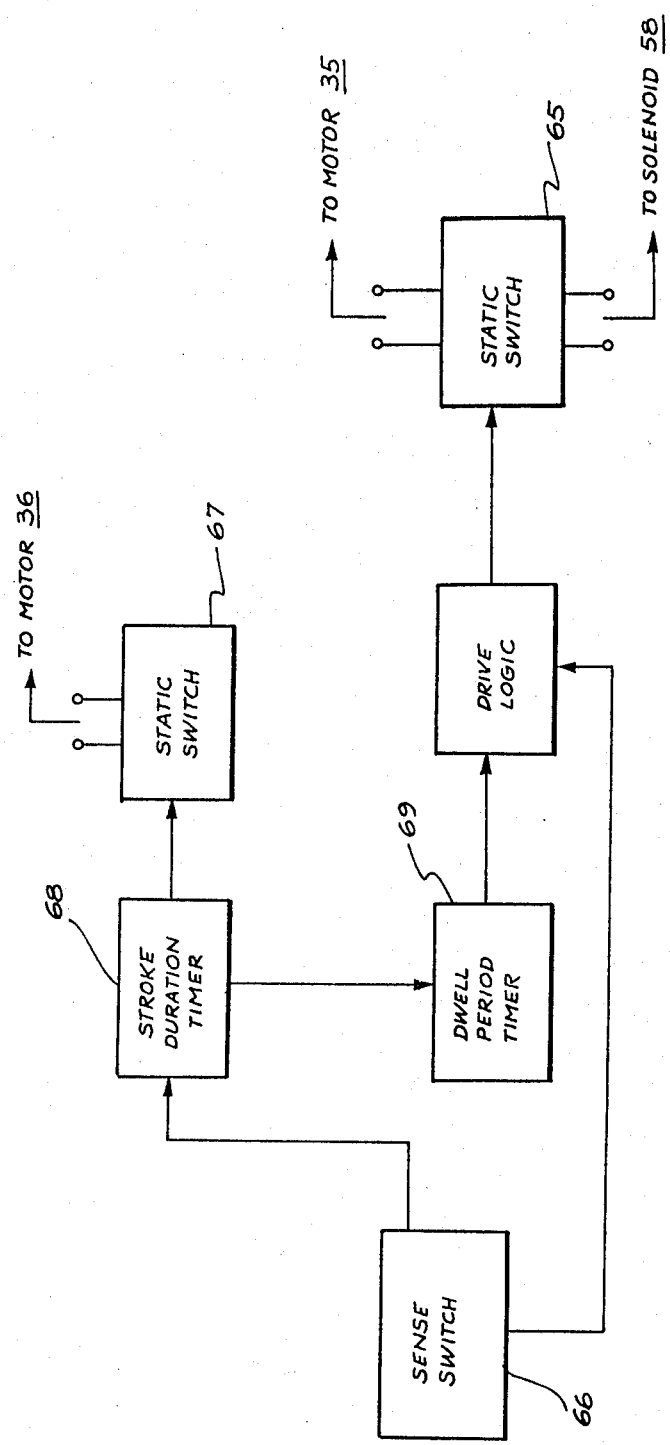
FIG. 7 shows a schematic block circuit diagram of electric control devices associated with the ventilator.

The operation of the ventilator as shown in FIGS. 1 to 6 is now described in conjunction with the circuit diagram of FIG. 7. As a starting point it is assumed that the chamber 20 is expanded and is about to commence a compression stroke. At this point in time the first motor 35 (FIG. 4) is energized by a static switch 65, and the solenoid 58 (FIG. 6) is simultaneously energized to cause closure of the valve 22. Energization of the first motor 35 causes rotation of the shaft 39 in a first direction and the chain limbs 42 and 46 to which the bridge 43 is connected are caused to descend. This causes compression of the chamber 20 until such time as a lower limit switch, i.e. a sense switch 66 (FIGS. 4 and 7) is actuated. Actuation of the sense switch 66 causes de-energization of both the motor 35 and solenoid 58. Simultaneously with de-energization of the first motor 35, the second motor 36 is energized via a static switch 67 and an expansion stroke timer 68 is enabled. When the second motor 36 is energized, its starting torque will exceed the free-wheeling torque of the de-energized first motor 35, and the shaft 39 will be caused to rotate in the second (opposite) direction to cause the chain limbs and bridge 33 to ascend. Thus, the chamber is caused to expand and the expansion stroke length will be determined by the period of time for which the second motor 36 remains energized. This period of time is controlled by selectively adjusting the time-out period of the expansion stroke timer 68 and, at the selected time-out instant, the second motor 36 is de-energized by way of the timer 68. The time-out period is adjusted to allow for momentum of the system and over-run of the second motor following its de-energization. Assuming for the time being a zero time delay or dwell time, when the second motor 36 is de-energized, the first motor 35 is again energized to cause reversal of the shaft rotation and downward movement of the bridge 33.

However, a dwell time may be introduced by way of a second (dwell) timer 69 which is enabled when the first timer 68 times-out. The second timer 69, which may be adjusted to provide a selected dwell time, inhibits energization of the motor 35 and hence delays commencement of the compression stroke until the second timer times-out. Thereafter, the compression stroke commences and the cycle repeats.

The timers 68 and 69 may be adjusted (by way of a potentiometer control not shown) during operation of the ventilator to vary the expansion/compression stroke lengths and to introduce a variable dwell time between completion of the expansion stroke and commencement of the compression stroke.

The sense switch 66 is positioned so as to be actuated before the chamber is fully compressed, so that the first motor is de-energized before the chamber is fully compressed. Energy in the system resulting from over-run of the first motor is then absorbed by final compression of the chamber, preparatory to the expansion stroke commencing, so that jarring of the system is reduced.

I claim as my invention:

1. A ventilator comprising an expansible chamber, port means for admitting gas passage into and from the chamber, first and second electric motors and a common output drive shaft to which the first and second motors are drivingly coupled, the respective motors being arranged when energized to impart rotational drive to the shaft in mutually opposite directions, means for effecting energization of the motors alternately, whereby the shaft is driven cyclically in mutually opposite rotational directions, motion translating means comprising at least one endless drive transmission element coupled to the shaft and to the chamber for imparting cyclic expansion and compression strokes to the chamber in dependence on the directions of rotation of the shaft, and means for determining the extent of the expansion and compression strokes imparted to the chamber.

2. A ventilator as claimed in claim 1 wherein the means for determining the expansion stroke of the chamber comprises means for adjustably timing the period of the expansion stroke imparted to the chamber, for effecting cessation of the expansion stroke after a predetermined period of time has elapsed and for effecting reversal of the direction of rotation of the shaft whereby the chamber is then caused to undergo a compression stroke.

3. A ventilator as claimed in claim 1 wherein the means for determining the extent of the compression stroke comprises means for sensing a predetermined compression of the chamber, for effecting cessation of the compression stroke and for effecting reversal of the direction of rotation of the shaft whereby the chamber is then caused to undergo an expansion stroke.

4. A ventilator as claimed in claim 1 wherein a speed reducing gear-box is interposed between the common shaft and the motion translating means.

5. A ventilator as claimed in claim 1 wherein the expansible chamber comprises a bellows which, in operation, is concertinaed during the compression stroke.

6. A ventilator as claimed in claim 1 and including a gas delivery fitting coupled to the chamber, the fitting having one leg connecting with the inlet/delivery port of the chamber, a second leg connectable to atmosphere and a third leg connectable to a patient circuit, and there being a spill valve located in the second leg.

7. A ventilator as claimed in claim 6 wherein the spill valve is connected to a solenoid actuator, the solenoid being arranged to be energized, whereby the valve is closed, during the period of energization of the first motor.

8. A ventilator as claimed in claim 7 wherein the solenoid is located within a retainer, the retainer containing a bath of oil, the solenoid being immersed at least in part within the oil bath, the retainer being closed by a diaphragm formed from a resilient material and a link coupling the solenoid to the valve by way of the diaphragm.

9. A ventilator comprising an expansible chamber, port means for admitting gas passage into and from the chamber, first and second electric motors and a common output drive shaft to which the first and second motors are drivingly coupled, the respective motors being arranged when energized to impart rotational drive to the shaft in mutually opposite directions, means for effecting energization of the motors alternately, whereby the shaft is driven cyclically in mutually opposite rotational directions, motion translating means comprising at least one endless drive transmission element coupled to the shaft and to the chamber for imparting compression strokes to the chamber with energization of the first motor and for imparting expansion strokes to the chamber with energization of the second motor, and means for determining the extent of the expansion and compression strokes imparted to the chamber.

10. A ventilator as claimed in claim 9 wherein the means for determining the extent of the expansion stroke comprises a timer device in circuit with the second motor for determining the period of time of energization of the second motor and hence the duration of the expansion stroke, and wherein a time delay device is located in circuit with the first motor for introducing a dwell time between de-energization of the second motor and energization of the first motor.

11. A ventilator as claimed in claim 10 wherein the timer device and the time delay device are both selectively adjustable.

12. A ventilator comprising an expansible chamber in the form of a bellows, a gas inlet/delivery port communicating with the chamber, first and second electric motors mounted to a common shaft, means for effecting cyclic energization of the respective motors whereby the shaft is driven cyclically in opposite directions, motion translating means comprising at least one endless positive drive transmission element coupling the shaft to the chamber for imparting cyclic expansion and compression strokes to the chamber in dependence on the direction of rotation of the shaft, means for adjustably timing the period of the expansion stroke imparted to the chamber and for effecting de-energization of the motor which effects said expansion stroke after a predetermined time has elapsed, and means for sensing a predetermined compression of the chamber and for effecting de-energization of the motor which effects said compression stroke.

* * * * *